(12) United States Patent
Zhou et al.

(10) Patent No.: US 6,620,796 B1
(45) Date of Patent: Sep. 16, 2003

(54) COMBINATORIAL LIBRARY SYNTHESIS AND PHARMACEUTICALLY ACTIVE COMPOUNDS PRODUCED THEREBY

(75) Inventors: Wenqiang Zhou, Montreal (CA); Yi Jin, Montreal (CA); Arlene Roland, Montreal (CA); Radhakrishnan Iyer, Shrewsbury, MA (US)

(73) Assignee: Micrologix Biotech Inc., Vancouver (CA)

( * ) Notice: Subject to any disclaimer, the term of this patent is extended or adjusted under 35 U.S.C. 154(b) by 0 days.

(21) Appl. No.: 09/709,246

(22) Filed: Nov. 8, 2000

Related U.S. Application Data

(60) Provisional application No. 60/172,508, filed on Dec. 17, 1999, and provisional application No. 60/164,036, filed on Nov. 8, 1999.

(51) Int. Cl.[7] .................. A61K 31/70; A61K 31/66; C07F 9/165
(52) U.S. Cl. ............... 514/45; 514/47; 514/48; 514/51; 514/81; 514/86; 514/263.23; 514/263.24; 514/263.37; 514/274; 536/26.7; 536/27.8; 544/243; 544/244; 544/276; 544/277; 544/310; 544/312; 544/317
(58) Field of Search ............... 514/81, 86, 45, 514/47, 48, 51; 544/243, 244; 536/26.7, 27.8

(56) References Cited

U.S. PATENT DOCUMENTS

| 5,614,504 A | 3/1997 | Hadden et al. ............ 514/45 |
| 5,773,431 A | 6/1998 | Javitt ............ 514/177 |

FOREIGN PATENT DOCUMENTS

| DE | 4111730 A1 | 4/1991 |
| FR | 2641537 A1 | 5/2001 |
| WO | WO 90/07520 | 7/1990 |
| WO | WO 92/18520 | 10/1992 |
| WO | WO 94/22864 | 10/1994 |
| WO | WO 95/32984 | 12/1995 |
| WO | WO 96/10030 | 4/1996 |
| WO | WO 96/39413 | 12/1996 |
| WO | WO 98/30575 | 7/1998 |
| WO | WO 99/64378 | 12/1999 |
| WO | WO 01/34622 | 5/2001 |

OTHER PUBLICATIONS

Moriguchi et al., Chemical Abstracts, vol. 131:228913, 1999.*
Ma et al., Chemical Abstracts, vol. 122:133624, 1995.*
Cummins et al., Chemical Abstracts, vol. 106:115671, 1987.*
Cummins et al., Chemical Abstracts, vol. 103:215702, 1985.*
Combinatorial Synthesis using nucleic acid–based NAB™ scaffold: parallel solid–phase synthesis of nucleotide libraries, W. Zhou et al., *Tetrahedron Letters*, 41:441–445, 2000.
Communications to the Editor: "Drug Leads from Combinatorial Phosphodiester Libraries", Peter W. Davis et al., *Med. Chem.*, 38:4363–4366, 1995.
International Search Report (May 2001).

* cited by examiner

*Primary Examiner*—Richard L. Raymond
(74) *Attorney, Agent, or Firm*—Seed Intellectual Property Law Group PLLC

(57) ABSTRACT

The invention provides new methods for synthesis of nucleotide-based compounds and new libraries of such compounds. Compounds of the invention are useful for a variety of therapeutic applications, including treatment of viral or bacterial infections and associated diseases and disorders.

19 Claims, 1 Drawing Sheet

COMBINATORIAL LIBRARY SYNTHESIS AND PHARMACEUTICALLY ACTIVE COMPOUNDS PRODUCED THEREBY

This application claims the benefit of U.S. Provisional Application Serial No. 60/164,036 filed Nov. 8, 1999, and U.S. Provisional Application Serial No. 60/172,508 filed Dec. 17, 1999, the teachings of which are incorporated herein by reference.

BACKGROUND OF THE INVENTION

1. Field of the Invention

The invention provides new methods for synthesis of nucleotide-based compounds and libraries of such compounds. Compounds of the invention are useful for a variety of therapeutic applications, including treatment of viral or bacterial infections and associated diseases and disorders.

2. Background

The important initial step in the development of therapeutic agents is the discovery of compounds that bind to a protein, enzyme or receptor of interest. Through careful structure/activity work of resulting active compounds, one arrives at a lead compound for further development into a clinical candidate. This traditional process of drug discovery is a long and arduous endeavor. Often it takes 10 to 15 years before a new drug makes it into the marketplace.

Recent advances in molecular biology and genomics have led to identification of new molecular targets for drug discovery. As a result of the limitation of traditional drug discovery, new approaches to the discovery of therapeutics have been developed. In the more modern approaches, large libraries of diverse compounds are synthesized by a number of methods and subjected to high throughput in vitro screening against a particular molecular target implicated in a disease. The active compounds so identified are then subjected to Structure-Activity Relationship (SAR) work to eventually identify the lead compound.

Modern drug discovery approaches entail the synthesis and screening of libraries of compounds. The design and synthesis of such libraries is often based on a unique molecular skeleton or scaffold. By incorporating a variety of structural elements into a scaffold, local as well as global molecular diversity can be achieved which facilitates specific interactions between a ligand and its receptor. The structural elements contribute to molecular diversity by variable spatial display of ionic, hydrogen-bonding, charge-transfer and van der Waals interactions thus allowing for the selection of the best 'fit' between the ligand and its receptor.

Traditionally, libraries have been constructed using solid-support synthesis methods, such as synthesis of a library on 'beads'. Solid support methods are useful because reactive products can be readily isolated in a relatively pure form by simply washing away excess reagents and solvents from the support matrix, something that is not possible with solution based methods.

One method for generating compound libraries utilizes a discrete compound approach. In the discrete compound approach, compounds are synthesized in parallel each in a separate reaction vessel. The identity of each compound is known or can be ascertained by analytical methods. Various methods for constructing discrete compound libraries are known in the art. For example, the Pin method (H. M. Geyson et al., PNAS, USA 81: 3998–4002 (1984)) utilizes polyethylene pins placed in a 96-well supporting block. Each pin is coated with polymeric material that is derivatized for anchoring functional groups. The reactions can be run on 100 nmol to 50 micromol scale and the products subjected to multiple biological assays. The Diversomer apparatus approach (S. H. Dewitt et al., PNAS, USA 90: 6909–6913 (1993)) utilizes a series of porous gas dispersion tubes which serve as containers for resin beads and reagents and solvents are placed in vials mounted on a reservoir block. The ends of the gas dispersion tubes are placed in the vials and the reagents are allowed to diffuse through the porous membrane and contact the resin support. The apparatus can be placed in a manifold with an injectable gasket. The porous frit apparatus utilizes each well of a deep well microtiter plate fitted with porous frits. The plate is clamped on to a viton gasket. In between synthetic steps in a sequence, the reaction solution can be drained and the resin rinsed by removal of the viton gasket. The spatially addressable, light directed parallel synthesis method utilizes a photolithographic method to synthesize 100,000 separate compounds. The synthesis is done on a silicon wafer (chip) that is functionalized to attach to a leader molecule which carries a photolabile protecting group at its reaction site. Once unmasked by illumination, the reactive group is unmasked which can then enter into a specific chemical reaction with a reactant. The library of compounds remain tethered to the solid support. The structure of the compound in each specific location is known.

Another method for generating compound libraries utilizes a mix and pool synthesis approach. This approach allows large libraries of compounds to be synthesized by pooling different sets of support-bound intermediates. However, this method only works when all of the reactants in a mixture have similar reactivities. Reaction conditions need to be optimized before attempting a split and pool strategy. This strategy has been used to synthesize libraries of peptides and oligonucleotides. Various mix and pool synthesis approaches are known in the art. For example, Houghten et al. (C. Pinilla et al., *Biopolymers, Pept. Sci.,* 37: 221–240 (1995), pioneered this approach by preparing pools of compounds that each contain structurally defined building blocks at one or two positions. Once the pool with the highest activity is identified in an in vitro assay, the deconvolution process begins. Iterative rounds of synthesis and biological assays are carried out until a molecule with the highest activity is identified. Modifications of this approach include the positional scanning approach developed by Houghten et al. (C. Pinilla et al., *Biopolymers, Pept. Sci.,* 37: 221–240 (1995) and the orthogonal approach developed by Tartar et al. (B. Deprez, et al., *J. Am. Chem. Soc.,* 117: 5405–5406 (1995). Another mix and pool synthesis approach utilizes beads encoded by oligonucleotides of known sequence to trace compounds.

Biological assays used to test the activity of compound libraries can be carried out with the compounds immobilized on a solid support or in solution. For example, a resin-bound library can be treated with a fluorescent-labeled receptor and the compound-bound receptors isolated using a fluorescence activated cell sorting instrument. Structure determination can be done, for example, by sequencing or mass spectrometry analysis. When assays are performed in solution, compounds need to be released from the solid support. A portion of the beads are released and contacted with the receptor. The active compounds are then traced back to the original bead. Structure determination can be performed by analytical methods.

See also: C. Pinilla et al., *Biopolymers, Pept. Sci* 37: 221–240 (1995); S. H. DeWitt et al., *PNAS, USA* 90: 6909–6913 (1993); B. Deprez et al., *J Am. Chem. Soc.* 117:

5405–5406 (1995); H. M. Geyson, et al. *PNAS, USA* 81: 3998–4002 (1984); G. Jung et al., *Angew. Chem. Intl. Ed. Engl.* 31: 367–383 (1992); M. R. Pavia, et al. *Bioorg. Med. Chem. Lett.* 3: 387–396 (1993); E. M. Gordon et al., *J. Med. Chem.* 37: 1385–1401 (1994); L. A. Thompson et al., *Chem. Rev.* 96: 555–600 (1996); S. Verma et al., *Annu. Rev. Biochem.* 67: 99–134 (1998); S. L. Beaueage et al., *Tetrahedron Lett.* 22: 1859–1862 (1981); R. P. Iyer et al., *In Comprehensive Natural Products,* D. H. R. Barton and K. Nakanishi Eds., Elsevier Science. Vol 7 (In press); A. D. Barone et al., *Nucl. Acids Res.* 12: 4051–4061 (1984); R. P. Iyer et al., *J. Am. Chem. Soc.* 112: 1253–54 (1990).

SUMMARY OF THE INVENTION

We have now found new nucleotide-based compounds that are useful for a variety of therapeutic applications, including to treat against viral or bacterial infections.

The invention also provides new methods for synthesis of nucleotide-based compounds and new libraries of such compounds. In particular, the invention provides new methods for construction of compound libraries utilizing a nucleic acid-based (NAB) scaffold. This approach enables incorporating structural elements that can provide both "sequence-specific" interactions (e.g., hydrogen-bonding interactions between nucleobases) as well as "shape-specific" motifs (e.g., bulges and stem-loop structures) that can allow specific recognition of other nucleic acids and proteins. Libraries based on NAB scaffold can potentially mimic the molecular recognition that exists between cellular macromolecules and biomolecules such as hormones, nucleotides and their receptors.

The invention provides methods for constructing compound libraries by solution-phase or solid-phase approaches. Preferred library syntheses of the invention are carried out on a solid support. Suitable solid supports include, for example, pins, beads, resins, chips, etc.

Preferred library syntheses of the invention include use of columns capable of agitation (e.g. spin or other rotation) and that may suitably contain a resin support material. Reactants are placed in the column, and the column preferably shaken or otherwise agitated during reaction. Additional reactants can be added to provide repeated reaction cycles. Reagents and reaction products also can be conveniently separated and removed from the column, e.g. by centrifuging a reaction column to facilitate removal (e.g. by filtration) of desired material.

Other aspects of the invention are disclosed infra.

DETAILED DESCRIPTION OF THE INVENTION

Figure 1:
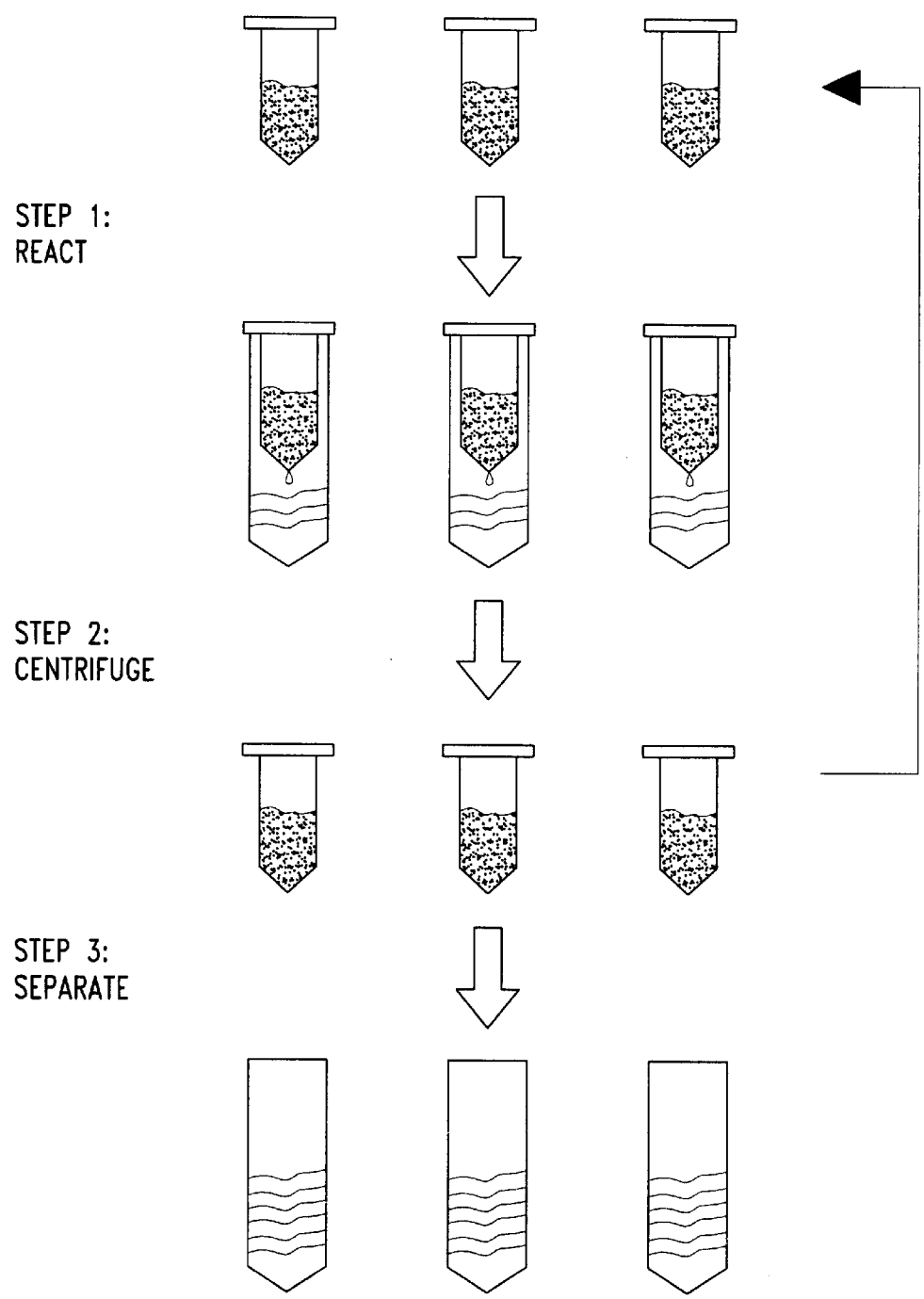
FIG. 1 provides a flow diagram for library assembly.

As discussed above, we have discovered new methods for construction of a compound library. Preferred library members include compounds of the following Formula I or I':

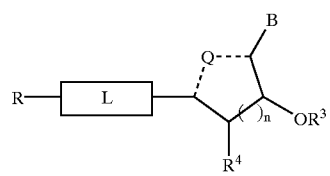

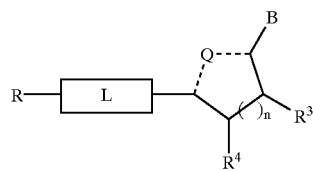

wherein

L is a linking group such as e.g. an amide, ester, diester or the like, or an optionally substituted alkylene (e.g. $C_{1-20}$ alkylene), optionally substituted alkenylene (e.g., $C_{2-20}$ alkenylene) or alkynylene (e.g., $C_{2-20}$ alkynylene) having such groups either as a chain member of pendant to the chain, and which may be optionally substituted with one or more substituents selected from a group consisting of O, S, Se, $NR^1NR^2$, $CR^1CR^2$, OR, SR and SeR (R, $R^1$ and $R^2$ defined below), or an enzymatically reactive (particularly, cleavable) moiety such as an amide, ester, and the like;

Q is carbon or a heteroatom such as O, S or N;

R is hydrogen or a hydroxyl group or a hydrophobic group, e.g. a moiety having from 1 to about 18 carbon atoms, such as optionally substituted alkyl, optionally substituted alkenyl, optionally substituted alkynyl, optionally substituted aralkyl, optionally substituted cycloalkyl, optionally substituted cycloalkenyl, optionally substituted carbocyclic aryl, an optionally substituted mononucleotide, an optionally substituted polynucleotide, or an optionally substituted heteroaromatic or heteroalicyclic group preferably having from 1 to 3 separate or fused ring and 1 to 3 N, O or S atoms;

$R^1$, $R^2$, $R^3$ and $R^4$ are each independently selected from a group as defined by R;

B is optionally substituted adenine, optionally substituted thymidine, optionally substituted cytosine or an optionally substituted guanine, preferably where the optional substituents are alkyl, carbocyclic aryl, or heteroaromatic or heteroalicyclic group preferably having from 1 to 3 separate or fused rings and 1 to 3 N, O or S atoms, or B is heteroaromatic or heteroalicyclic group other than an adenine, thymidine, cytosine or guanine and preferably has from 1 to 3 separate or fused rings and 1 to 3 N, O or S atoms;

n is an integer of from 1 to 5 and where n is greater than 1 designates that corresponding additional carbon ring or acyclic members are present (i.e. where n is 2 an additional carbon ring member (to form a 6-membered ring) or acyclic carbon is present; where n is 3, two additional carbon ring members (to form a 7-membered ring) or acyclic carbon is present, and so on);

and pharmaceutically acceptable salts thereof.

In the above Formulae I and I', it is understood that the dashed line indicates the ring may be in the open or closed configuration.

The depicted sugar group may be natural or modified (e.g. synthetic) form, or in an open chain form (where one of the depicted ring bonds would not be present).

Preferred R groups of compounds of formulae I and I' include cyclic groups, particularly alicyclic groups that may comprise one or more single or polycyclic rings, particularly a bridged or fused ring structure, with 0, 1 or 2 endocyclic carbon-carbon double bonds. Additional preferred R groups include heteroalicyclic moieties, particularly heteroalicyclic groups having from 5 to about 8 ring member, preferably with one or two O, N or S ring members, particularly one or two oxygen ring members.

Preferred compounds of the invention include those of formulae I and I' where the nucleoside is linked to the R group via a phosphorous group at the 5' end. Other dephospholinkers such as carbonates, carbamates, ureas, acetals, etc., may also be used. Such linkages could also be established via the 2' or 3' sites of the nucleoside. When R is a nucleoside, linkages can be via 5' to 3', 5' to 5', 3' to 3', 2' to 5' and 2' to 2', or any combination thereof, of the participating nucleosides.

Preferred library members include compounds of the following Formula II or II':

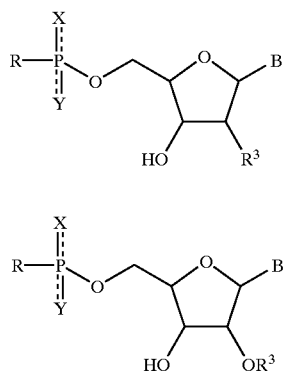

wherein
- X and Y are each independently selected from a group consisting of O, S, Se, NR$^1$NR$^2$, CR$^1$CR$^2$, OR, SR and SeR, or one or both of X and Y are an enzymatically reactive (particularly, cleavable) moiety such as an amide, ester, and the like;
- R is a hydrophobic group, e.g. a moiety having from 1 to about 18 carbon atoms, such as optionally substituted alkyl, optionally substituted alkenyl, optionally substituted alkynyl, optionally substituted aralkyl, optionally substituted cycloalkyl, optionally substituted cycloalkenyl, optionally substituted carbocyclic aryl, an optionally substituted mononucleotide, an optionally substituted polynucleotide, or an optionally substituted heteroaromatic or heteroalicyclic group preferably having from 1 to 3 separate or fused ring and 1 to 3 N, O or S atoms;
- R$^1$, R$^2$ and R$^3$ are each independently selected from a group as defined by R;
- B is optionally substituted adenine, optionally substituted thymidine, optionally substituted cytosine or an optionally substituted guanine, preferably where the optional substituents are alkyl, carbocyclic aryl, alkynyl, or heteroaromatic or heteroalicyclic group preferably having from 1 to 3 separate or fused rings and 1 to 3 N, O or S atoms, or any heterocyclic structure that is covalently linked to the sugar ring;

and pharmaceutically acceptable salts thereof.

In the above Formulae II and II', it is understood that the dashed line extending to each of the substituents X and Y designates that one, but not both, of X and Y may have an additional chemical bond (i.e. a double bond).

The depicted sugar group may be natural or modified (e.g. synthetic) form, or in an open chain form (where one of the depicted ring bonds would not be present).

Preferred R groups of compounds of formulae II and II' include cyclic groups, particularly alicyclic groups that may comprise one or more single or polycyclic rings, particularly a bridged or fused ring structure, with 0, 1 or 2 endocyclic carbon-carbon double bonds. Additional preferred R groups include heteroalicyclic moieties, particularly heteroalicyclic groups having from 5 to about 8 ring member, preferably with one or two O, N or S ring members, particularly one or two oxygen ring members.

As mentioned above, either one or both of X and Y may be an enzymatically reactive group, i.e. the group may be cleavable or otherwise reactive in vivo upon administration to a mammal, particularly a human. Preferred enzymatically reactive groups include e.g. amides (which may be cleaved in vivo with an amidase), esters (which may be cleaved in vivo with an esterase), and acetal and ketal groups.

Preferred compounds of the invention include those of formulae II and II' where the nucleoside is linked to the R group via a phosphorous group at the 5' end. Other dephospholinkers such as carbonates, carbamates, ureas, acetals, etc., may also be used. Such linkages could also be established via the 2' or 3' sites of the nucleoside. When R is a nucleoside, linkages can be via 5' to 3', 5' to 5', 3' to 3',2' to 5' and 2' to 2', or any combination thereof, of the participating nucleosides.

Preferably, compounds of the invention will be present in enantiomerically enriched mixtures, i.e. where one enantiomer is present in a greater amount than other stereoisomer (s) of the compound, particularly where one enantiomer is present in amount of at least about 60 mole percent, relative to all stereoisomers present of the compound; preferably where one enantiomer is present in amount of at least about 70 or 80 mole percent, relative to all stereoisomers present of the compound; still more preferably where one enantiomer is present in amount of at least about 85, 90, 92, 95, 96, 97, 98 or 99 mole percent, relative to all stereoisomers present of the compound Preferred compounds of the invention include those of the following Formulae IIA and IIA', having the depicted configurations:

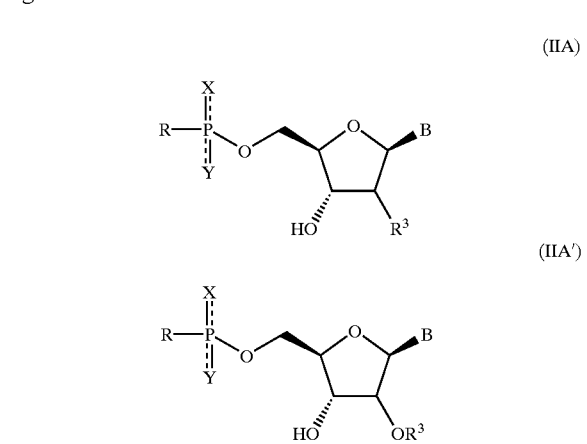

X, Y, R, R$^1$, R$^2$, B, R$^3$ and n are the same as defined above for Formulas II and II'; and pharmaceutically acceptable salts thereof.

In the above Formulae IIA and IIA', it is understood that the dashed line extending to each of the substituents X and Y designates that one, but not both, of X and Y may have an additional chemical bond (i.e. a double bond).

In the above Formulae IIA and IIA', the depicted sugar group may be natural or modified (e.g. synthetic) form, or in an open chain form (where one of the depicted ring bonds would not be present).

In the above Formulae I, I', II, II', IIA and IIA', alkyl groups preferably contain from 1 to about 18 carbon atoms, more preferably from 1 to about 12 carbon atoms and most preferably from 1 to about 6 carbon atoms. Specific examples of alkyl groups include, for example, methyl, ethyl, n-propyl, isopropyl, n-butyl, t-butyl, isobutyl, pentyl, hexyl, heptyl, octyl, nonyl, decyl etc.

In the above Formulae I, I', II, II', IIA and IIA', aralkyl groups include the above-listed alkyl groups substituted by a carbocyclic aryl group having 6 or more carbons, for example, phenyl, naphthyl, phenanthryl, anthracyl, etc.

In the above Formulae I, I', II, II', IIA and IIA', cycloalkyl groups preferably have from 3 to about 8 ring carbon atoms, e.g. cyclopropyl, cyclopentyl, cyclohexyl, cycloheptyl, 1,4-methylenecyclohexane, adamantyl, cyclopentylmethyl, cyclohexylmethyl, 1- or 2-cyclohexylethyl and 1-, 2- or 3-cyclohexylpropyl, etc.

In the above Formulae I, II', II, II', IIA and IIA', exemplary heteroaromatic and heteroalicyclic group include pyridyl, pyrazinyl, pyrimidyl, furyl, pyrrolyl, thienyl, thiazolyl, oxazolyl, imidazolyl, indolyl, benzothiazolyl, tetrahydrofuranyl, tetrahydropyranyl, piperidinyl, morpholino and pyrrolidinyl.

Mononucleotides of compounds of the invention (compounds of Formulae I, I', II, II', IIA and IIA') invention include adenine, cytosine, guanosine and thymidine.

Polynucleotides of compounds of the invention (compounds of Formulae I, I', II, II', IIA and IIA') preferably contain from about 1 to about 20 mononuculeotides, more preferably from 1 to about 10 mononuculeotides and still more preferably from 1 to about 5 mononuculeotides. The polynucleotides are suitably constructed such that the 5' group of one mononucleotide pentose ring is attached to the 3' group of its neighbor in one direction via, for example, a phosphodiester or a phosphorthioate internucleotide linkage.

Sugar groups of compounds of the invention may be comprised of mono-, di-, oligo- or poly-saccharides wherein each monosaccharide unit comprises from 3 to about 8 carbons, preferably from 3 to about 6 carbons, containing polyhydroxy groups or polyhydroxy and amino groups. Non-limiting examples include glycerol, ribose, fructose, glucose, glucosamine, mannose, galactose, maltose, cellobiose, sucrose, starch, amylose, amylopectin, glycogen and cellulose. The hydroxyl and amino groups are present as free or protected groups containing e.g. hydrogens and/or halogens. Preferred protecting groups include acetonide, t-butoxy carbonyl groups, etc. Monosaccharide sugar groups may be of the L or D configuration and a cyclic monosaccharide unit may contain a 5 or 6 membered ring of the α or β conformation. Disaccharides may be comprised of two identical or two dissimilar monosaccharide units. Oligosaccharides may be comprised of from 2 to 10 monosaccharides and may be homopolymers, heteropolymers or cyclic polysugars. Polysaccharides may be homoglycans or heteroglycans and may be branched or unbranched polymeric chains. The di-, oligo- and poly-saccharides may be comprised of 1→4, 1→6 or a mixture of 1→4 and 1→6 linkages. The sugar moiety may be attached to the link group through any of the hydroxyl or amino groups of the carbohydrate.

Preferred compounds of the invention comprise R groups containing one of the hydrophobic structures represented in Table 1 below.

Preferred library syntheses of the invention are carried out on a solid support. Suitable solid supports include, for example, pins, beads, resins, chips, etc. Particularly preferred methods are those carried out using beads as the solid support.

Phospholinked compounds of the invention can be prepared as generally depicted in Scheme I. In addition to the synthetic route depicted in Scheme 1, library compounds may also be assembled using a phosphodiester approach, a phosphortriester approach and/or the H-phosphonate methodology (R. P. Iyer et al. In Comprehensive Natural Products, D. H. R. Barton and K. Nakanishi Eds., Elsevier Science Vol 7, in press). In Scheme I below, preferred stereoisomers and substituent groups are depicted, although it is understood that other compounds of the invention can be produced by the same or similar procedures.

SCHEME I

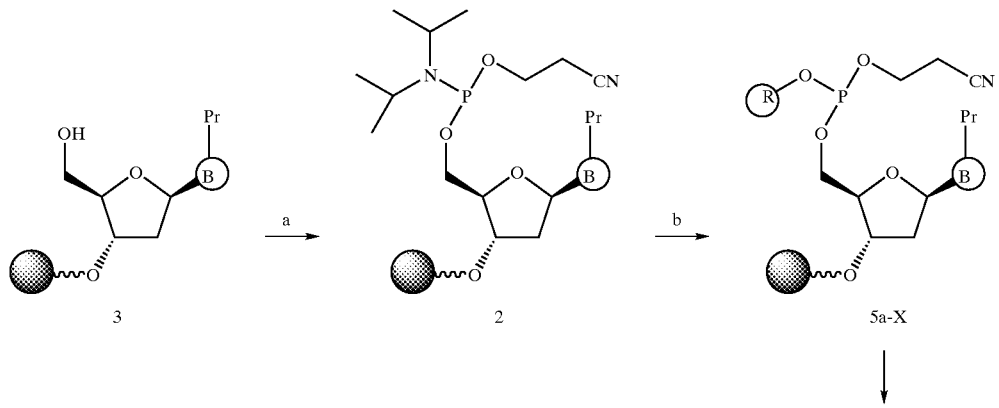

-continued

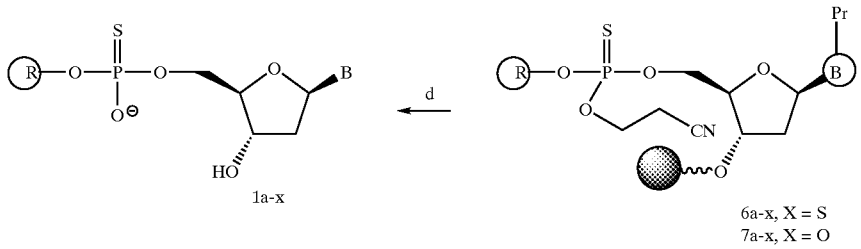

1a-x 6a-x, X = S
7a-x, X = O

Pr = protecting group
B = A, C, G or T
R = see description in table 1
a = Bis-(N,N-diisopropylamino)-2-cyanoethylphosphine,
    diisopropylammonium tetrazolide in CH$_2$Cl$_2$
b = ROH (4a-f), tetrazole in CH$_3$CN
c = 3 H-1,2-benzodithiole-3-one-1, 1-dioxide in CH$_3$CN (6a-x),
    or I$_2$ in Pyr/H$_2$O/THF (7a-x)
d = 28% NH$_4$OH Scheme I shows the preparation of library compounds using phosphoramidite chemistry (S. L. Beaueage et al., Tetrahedron Lett. 22: 1859–1862 (1981); R. P. Iyer et al., In Comprehensive Natural Products, D. H. R. Barton and K. Nakanishi Eds. Elsevier Science. Vol. 7 (in press)). A key synthon is the solid-support-bound phosphoramidite, shown as compound 2 of Scheme I. Compound 2 can be prepared by 5'-phosphitylation of controlled-pore-glass (CPG)-bound nucleoside, shown as compound 3 of Scheme I. β-cyanoethyl bis(N,N-diisopropylamino)phosphine (CNP) in the presence of N,N-diisopropylammonium tetrazolide was used as the phosphitylating reagent, which produced byproducts soluble in methylene chloride. The reaction mixture was filtered and a quantitative yield of compound 2 was obtained. Each CPG-bound nucleoside phosphoramidite (compound 2) could be stored in vacuo for subsequent use in library synthesis.

The library synthesis was performed in a parallel format using QIAquick® spin columns (Quiagen) each of which was equipped with a sepharose resin supported by a nitrocellulose filter at the bottom (FIG. 1). The reactants were placed in the spin columns and the contents shaken were shaken during the reaction. The columns were then placed in a recepticle vial and centrifuged allowing facile filtration of the mixture into the recepticle. The next reactant was then added to the spin columns and the process repeated until the library synthesis was complete.

Typically for the synthesis of the library (Scheme I, FIG. 1), a measured amount of CPG-bound phosphoramidite (compound 2) was transferred to a series of spin columns. The alcohols 4a–f were added to the spin columns along with tetrazole in acetonitrile and incubated for 5 minutes. The spin columns were then centrifuged to separate out the unreacted materials and byproducts from the support-bound coupled product 5a–x as a mixture of Rp and Sp diastereomers. The oxidative sulfurization of 5a–x was performed using either 3H-1,2-benzodithiole-3-one-1,1-dioxide (0.1 M in acetonitrile) or I$_2$ solution (0.02 M in Pyridine/H$_2$O/tetrahyrofuran) to produce the support bound phosphotriesters 6a–x or 7a–x, respectively. The support-bound library was heated with NH$_4$OH (28%, 55° C., 5 hours) to remove the crude diesters. Each of the crude products were passed through a Sep-Pak cartridge® (Waters) to give products 1a–x. It is to be noted that oxidative sulfurization and oxidation can also be carried out using other sulfurizing and oxidizing agents.

Table 1 below shows the members of a representative 24-member library. The library members were analyzed using reversed-phase HPLC and determined to be 90–95% pure.

Table 1. Representative Library members (1a–x), and their HPLC retention time (R$_t$ min). R=hydrophobic group, Pdt=product, B=nucleobase, A=Adenine, C=cytosine, G=guanine, T=Thymine.

TABLE 1

Representative Library members (1a-x), and their HPLC retention time
(R$_t$ min). R = hydrophobic group, Pdt = product, B = nucleobase, A = Adenine,
C = cytosine, G = guanine, T = Thymine

| B | Pdt | R$_t$ | Pdt | R$_t$ | Pdt | R$_t$ | Pdt | R$_t$ | Pdt | R$_t$ | Pdt | R$_t$ |
|---|---|---|---|---|---|---|---|---|---|---|---|---|
| A | 1a | 30.5 | 1e | 34.3 | 1i | 47.8 | 1m | 45.0 | 1q | 36.0 | 1u | 43.3 |
| C | 1b | 28.6 | 1f | 33.3 | 1j | 47.5 | 1n | 44.1 | 1r | 35.1 | 1v | 42.7 |

TABLE 1-continued

Representative Library members (1a-x), and their HPLC retention time
($R_t$ min). R = hydrophobic group, Pdt = product, B = nucleobase, A = Adenine,
C = cytosine, G = guanine, T = Thymine

| B | Pdt | $R_t$ | Pdt | $R_t$ | Pdt | $R_t$ | Pdt | $R_t$ | Pdt | $R_t$ | Pdt | $R_t$ |
|---|---|---|---|---|---|---|---|---|---|---|---|---|
| G | 1c | 28.1 | 1g | 31.7 | 1k | 46.5 | 1o | 42.9 | 1s | 33.6 | 1w | 41.0 |
| T | 1d | 29.7 | 1h | 37.8 | 1l | 48.2 | 1p | 47.4 | 1t | 38.2 | 1x | 46.5 |

When prepared as a mixture, compound libraries of the invention preferably will contain at least about 2, 3, 4 or 5 distinct compounds, more preferably at least about 10 distinct compounds, still more preferably at least about 20, 30, 40, 50, 60, 70, 80, 90 or 100 compounds, and may contain 200, 300, 400 or 500 or more compounds.

Table 2 shows examples of additional representative hydrophobic groups which may be linked to the 5' end of ribo- and deoxyribonucleosides via linkages. Specific examples of hydrophobic groups include saturated and unsaturated acyclic and cyclic alcohols, aromatic and heterocyclic alcohols. Exemplary groups demonstrated in table 2 include primary and secondary alcohols. However, one of skill in the art will recognize that the methods may be extended to other kinds of structural variants, specifically those hydrophobic groups bearing multiple functionalities, such as for example, ether, keto, amino, halo in addition to the hydroxy groups. Further, one of skill in the art would also recognize that the methods disclosed may be useful for linkage to additional available sites such as the 3' and 2' sites.

TABLE 2

| open-chain alcohol | cyclic primary alcohol | cyclic secondary alcohol | aromatic alcohol |
|---|---|---|---|

TABLE 2-continued

| open-chain alcohol | cyclic primary alcohol | cyclic secondary alcohol | aromatic alcohol |
|---|---|---|---|
| 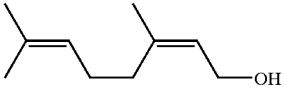 iv | 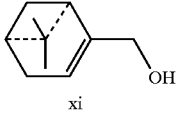 xi | 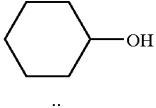 xvii | 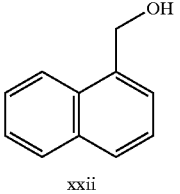 xxii |
| 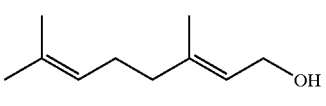 v | 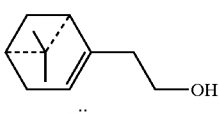 xii | 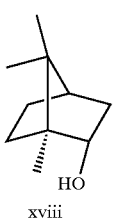 xviii | 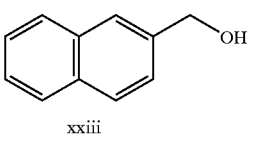 xxiii |
| 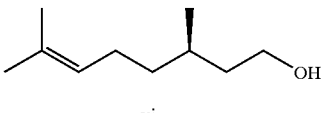 vi | 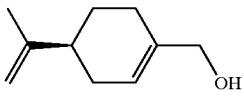 xiii | | 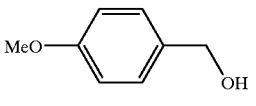 xxiv |
| 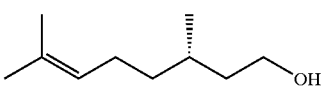 vii | 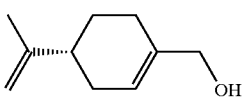 xiv | 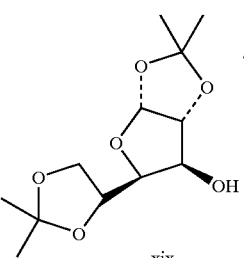 xix | 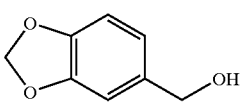 xxv |

Compounds of the invention (compounds of Formulae I, I', II, II', IIA and IIA') will be useful for a variety or therapeutic applications, such as bacterial or viral infections. For example, methods of the invention include treatment against infections and diseases associated with viruses, which methods in general comprise administration of a therapeutically effective amount of one or more compounds of Formulae I, I', II, II', IIA or IIA', to virally infected cells, such as mammalian cells, particularly human cells.

More specifically, the invention includes methods of treatment of a mammal susceptible to (prophylactic treatment) or suffering from a disease associated with DNA and RNA viruses; examples include viruses of the herpes family, e.g. herpes simplex viruses (HSV) including herpes simplex 1 and 2 viruses (HSV 1, HSV 2), varicella zoster virus (VZV; shingles), human herpes virus 6, cytomegalovirus (CMV), Epstein-Barr virus (EBV), and other herpes virus infections such as feline herpes infections, and diseases associated with hepatitis viruses including hepatitis B (HBV) and C (HCV) viruses. Examples of clinical conditions which are caused by such viruses include herpetic keratitis, herpetic encephalitis, cold sores and genital infections (caused by herpes simplex), chicken pox and shingles (caused by varicella zoster) and CMV-pneumonia and retinitis, particularly in immunocompromised patients including renal and bone marrow transplant and patients with Acquired Immune Deficiency Syndrome (AIDS).

Epstein-Barr virus can cause infectious mononucleosis, and is also suggested as the causative agent of nasopharyngeal, immunoblastic lymphoma and Burkitt's lymphoma.

Compounds of the invention also will be useful for cancer therapy, particularly to treat solid tumors, such as may be present in the liver, lung, brain or other tissue.

Compounds of the invention also will be useful for treatment against bacterial infections, including both Gram positive and Gram negative bacteria, and mycobacteria.

Administration of compounds of the invention may be made by a variety of suitable routes including oral, topical (including transdermal, buccal or sublingual), nasal and parenteral (including intraperitoneal, subcutaneous, intravenous, intradermal or intramuscular injection) with oral or parenteral being generally preferred. It also will be appreciated that the preferred method of administration and dosage amount may vary with, for example, the condition and age of the recipient.

Compounds of the invention may be used in therapy in conjunction with other pharmaceutically active medicaments, such as another anti-viral agent, or an anti-cancer agent. Additionally, while one or more compounds of the invention may be administered alone, they also may be present as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

Therapeutic compounds of the invention also may be incorporated into liposomes. The incorporation can be carried out according to known liposome preparation procedures, e.g. sonication and extrusion. Suitable conventional methods of liposome preparation are also disclosed in e.g. A. D. Bangham et al., *J. Mol. Biol.,* 23:238–252 (1965); F. Olson et al., *Biochim. Biophys. Acta,* 557:9–23 (1979); F. Szoka et al., *Proc. Nat. Acad. Sci.,* 75:4194–4198 (1978); S. Kim et al., *Biochim. Biophys. Acta,* 728:339–348 (1983); and Mayer et al., *Biochim. Biophys. Acta,* 858:161–168 (1986).

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests.

All documents mentioned herein are incorporated herein by reference.

The present invention is further illustrated by the following examples. These examples are provided to aid in the understanding of the invention and are not to be construed as limitations thereof.

EXAMPLE 1

Preparation of the CPG-bound Phosphoramidite (Compound 2) 2a–d

Each of the CPG-bound nucleosides 3a–d (3 g, 0.228 mmol), along with bis-(N,N-diisopropylamino)-2-cyanoethylphosphine (0.36 mL, 1.14 mmol), bisdiisopropylammonium tetrazolide (850 mg) in methylene chloride (50 mL) were placed in flasks and shaken at 30° C. overnight. The CPG-bound phosphoramidite 2a–d was collected by filtration and washed sequentially with $CH_2Cl_2$ (200 mL), $CH_3CN$ (100 mL) and anhydrous ether (50 mL) and dried in vacuo.

EXAMPLE 2

Synthesis of a 24 Member Library 1–6, a–d (Products 1a–x) (See Scheme 1, Table 1)

Step 1: The CPG-bound phosphoramidites 2a–d (5 mmol) were placed in spin columns. A solution of tetrazole (0.5 mL, 0.45 M in $CH_3CN$) was added. The appropriate alcohols 4a–f (25 mmol) were added to the reaction mixture. The mixture was shaken for five minutes and the solvent removed by centrifugation and decanted. The CPG was then washed with $CH_3CN$ (2×0.5 mL).

Step 2: The CPG was then soaked in a solution of 3H-1,2-benzodithiole-3-one-1, 1-dioxide in $CH_3CN$ (0.1 M, 0.5 mL). The mixture was shaken at room temperature for five minutes. The solvent was removed and the CPG washed with acetonitrile (2×0.5 mL) and dried under argon.

Step 3: The CPG was transferred to a conical screwcap tube (1.5 mL, VWR) and ammonium hydroxide (28%, 1.5 mL) added. The mixture was heated at 55° C. for 4 hours. The suspension was cooled and centrifuged. The supernatant containing the desired products were collected in a speed vac to give 1–6, a–d (products 1a–x).

Typical spectral data are as follows:

Nucleoside 1a: $^1$H NMR ($D_2O$): δ8.44 (d, 1H, J=9.2 Hz), 8.21 (s, 1H), 6.44–6.47 (m, 1H), 4.24 (s, 1H), 3.96–4.06 (m, 2H), 3.55–3.64 (m, 2H), 2.81–2.88 (m, 1H), 2.57–2.62 (m, 1H), 1.30–1.35 (m, 2H), 1.04–1.09 (m, 2H), 0.67 (t, 3H, $J_1$=7.5 Hz, $J_2$=7.3 Hz) ppm; $^{31}$P NMR ($D_2O$): δ58.97, 58.64 ppm; MS (negative mode): calcd. for $C_{14}H_{21}N_5O_5PS$, 402 (M); found m/z, 402.

Nucleoside 1b: $^1$H NMR ($D_2O$): δ8.05 (d, 1H, J=7.7 Hz), 6.24 (t, 1H, J=6.6 Hz), 6.10 (d, 1H, J=7.8 Hz), 4.50–4.53 (m, 1H), 4.19 (s, 1H), 4.03–4.12 (m, 2H), 3.84–3.88 (m, 2H), 2.40–2.45 (m, 1H), 2.24–2.29 (m, 1H), 1.51–1.57 (m, 2H), 1.25–1.33 (m, 2H), 0.83 (t, 3H, $J_1$=7.5 Hz) ppm; $^{31}$P NMR ($D_2O$): δ58.96 ppm; MS (negative mode): calcd. for $C_{13}H_{21}N_3O_6PS$, 378 (M); found m/z, 378.

Nucleoside 1c: $^1$H NMR ($D_2O$): δ8.04 (d, 1H, J=5.4 Hz), 6.24–6.28 (m, 1H), 4.19 (s, 1H), 3.96–4.05 (m, 2H), 3.63–3.68 (m, 2H), 2.78–2.85 (m, 1H), 2.47–2.52 (m, 1H), 1.34–1.41 (m, 2H), 1.07–1.13 (m, 2H), 0.71 (t, 3H, $J_1$=7.5 Hz) ppm; $^{31}$P NMR ($D_2O$): δ58.91, 58.61 ppm; MS (negative mode): calcd. for $C_{14}H_{21}N_5O_6PS$, 418 (M); found m/z, 418.

Nucleoside 1d: $^1$H NMR ($D_2O$): δ7.71 (s, 1H), 6.28 (t, 1H, J=7.0 Hz), 4.53–4.54 (m, 1H), 4.14–4.17 (t, 1H, J=2.5 Hz), 4.06–4.07 (m, 2H), 3.83–3.88 (m, 2H), 2.30–2.33 (m, 2H), 1.90 (d, 3H, J=4.4 Hz), 1.50–1.56 (m, 2H), 1.24–1.31 (m, 2H), 0.81 (t, 3H, $J_1$=7.4 Hz) ppm; $^{31}$P NMR ($D_2O$): δ58.32, 58.24 ppm; MS (negative mode): calcd. for $C_{14}H_{22}N_2O_7PS$, 393 (M); found m/z, 393.

Nucleoside 1e: $^1$H NMR ($D_2O$): δ8.44 (d, 1H, J=10 Hz), 8.23 (s, 1H), 6.44–6.47 (m, 1H), 4.25 (s, 1H), 3.94–4.06 (m, 2H), 3.32–3.46 (m, 2H), 2.83–2.89 (m, 1H), 2.57–2.62 (m, 1H), 1.84–1.90 (m, 1H), 1.40–1.44 (m, 2H), 1.29–1.30 (m, 4H), 0.82–0.90 (m, 2H) ppm; $^{31}$P NMR ($D_2O$): δ58.73, 58.28 ppm.

Nucleoside 1f: $^1$H NMR ($D_2O$): δ8.7.94 (d, 1H, J=7.6 Hz), 6.23 (t, 1H, J=6.7 Hz), 6.03 (d, 1H, J=7.8 Hz), 4.51 (d, 1H, J=2.9 Hz), 4.17 (s, 1H), 4.03 –4.08 (m, 2H), 3.67–3.70 (m, 2H), 2.38–2.42 (m, 1H), 2.20–2.25 (m, 1H), 2.06–2.1 (m, 4H), 1.61 (br, 1H), 1.45, 1.46 (2×S, 4H) 1.14–1.16 (m, 2H) ppm; $^{31}$P NMR ($D_2O$): δ☐58.79, 58.70 ppm.

Nucleoside 1g: 1H NMR ($D_2O$): δ8.10 (d, 1H, J=7.3 Hz), 6.24–6.27 (m, 1H), 4.19 (s, 1H), 3.97–4.04 (m, 2H), 3.38–3.52 (m, 2H), 2.79–2.86 (m, 1H), 2.48–2.53 (m, 1H), 1.89–1.94 (m, 1H), 1.45–1.50 (m, 2H), 1.34 (bs, 4H), 0.87–1.00 (m, 2H) ppm; $^{31}$P NMR ($D_2O$): δ58.64, 58.23 ppm.

Nucleoside 1h: $^1$H NMR ($D_2O$): δ7.71 (s, 1H), 6.28 (t, 1H, J=7.0 Hz), 4.55–4.56 (m, 1H), 4.15 (d, 1H, J=2.2 Hz), 4.04–4.10 (m, 2H), 3.66–3.74 (m, 2H), 2.31–2.34 (m, 2H), 2.08–2.14 (m, 1H), 1.90 (d, 3H, J=5.5 Hz), 1.61–1.63 (m, 2H), 1.46–1.47 (m, 4H), 1.12–1.17 (m, 2H) ppm; $^{31}$P NMR (D$_2$O): δ58.76, 58.61 ppm.

Nucleoside 1k: $^1$H NMR (D$_2$O): δ8.06–8.08 (m, 1H), 6.24 (t, 1H, J=6.6 Hz), 6.11–6.13 (m, 1H), 5.26 (s, 1H), 4.50–4.53 (m, 1H), 4.18 (d, 1H, J=2.0 Hz), 4.05–4.12 (m, 2H), 3.78–3.88 (m, 2H), 2.41–2.45 (m, 1H), 2.22–2.30 (m, 4H), 2.09–2.18 (m, 2H), 1.95–2.01 (m, 2H), 1.18 (s, 3H), 1.00 (d, 1H, 3.9 Hz), 0.71 (d, 3H, 2.0 Hz) ppm; $^{31}$P NMR (D$_2$O): δ58.91, 58.67 ppm.

Nucleoside 1l: $^1$H NMR (D$_2$O): δ7.74 (d, 1H, J=6.7 Hz), 6.30 (t, 1H, J=7.0 Hz), 5.23 (s, 1H), 4.54 (d, 1H, J=2.1 Hz), 4.14 (s, 1H), 4.06–4.08 (m, 2H), 3.80–3.84 (m, 2H), 2.22–2.35 (m, 5H), 2.07–2.17 (m, 2H), 2.00 (s, 1H), 1.86–1.92 (m, 4H), 1.24 (d, 1H, J=6.8 Hz), 1.16 (s, 3H), 1.09 (d, 1H, J=6.8 Hz), 0.97 (d, 1H, J=8.3 Hz), 0.69 (s, 3H) ppm; $^{31}$P NMR (D$_2$O): δ58.91, 58.67 ppm.

Nucleoside 1n: $^1$H NMR (D$_2$O): δ7.93 (d, 1H, J=7.6 Hz), 6.22 (t, 1H, J=6.3 Hz), 6.01–6.03 (m, 1H), 5.70 (s, 1H), 4.48–4.50 (m, 1H), 4.22, 4.23 (2×s, 2H), 4.16 (d, 1H, J=1.9 Hz), 4.05–4.10 (m, 2H), 2.37–2.42 (m, 1H), 2.18–2.22 (m, 1H), 1.98–2.06 (m, 4H), 1.81–1.87 (t, 1H, J=14.7 Hz), 1.66 (s, 3H), 1.30–1.35 (m, 1H) ppm; $^{31}$P NMR (D$_2$O): δ59.69, 59.15 ppm.

Nucleoside 1p: $^1$H, NMR (D$_2$O): δ7.71 (d, 1H, J=5.1 Hz), 6.27 (t, 1H, J=6.9 Hz), 5.71 (s, 1H), 4.54 (t, 1H, J=2.5 Hz), 4.25 (m, 2H), 4.15 (s, 1H), 4.08 (m, 2H), 2.29–2.33 (m, 2H), 2.00–2.07 (m, 4H), 1.86–1.89 (m, 4H), 1.71–1.76 (m, 1H), 1.68 (s, 3H), 1.31–1.38 (m, 1H) ppm; $^{31}$P NMR (D$_2$O): δ59.09, 59.00 ppm.

Nucleoside 1r: $^1$H NMR (D$_2$O): δ7.95 (d, 1H, J=7.6 Hz), 6.20–6.24 (q, 1H), 6.04–6.06 (dd, 1H, J$_1$=7.6 Hz), 5.96–5.99 (dd, 1H, J$_1$=12.9 Hz, J$_2$=3.5 Hz), 4.80–4.90 (dd, 1H), 4.48–4.50 (m, 1H), 4.32–4.46 (m, 2H), 4.14–4.18 (m, 2H), 4.04–4.10 (m, 2H), 3.95–3.98 (m, 1H), 2.40–2.46 (m, 1H), 2.17–2.25 (m, 1H), 1.89 (s, 4H), 1.45 (d, 3H, 9.2 Hz), 1.38 (d, 3H, 4.8 Hz), 1.28 (d, 3H, 2.5 Hz), 1.24 (d, 3H, 9.2 Hz) ppm; $^{31}$P NMR (D$_2$O): δ59.75, 59.24 ppm.

Nucleoside 1t: $^1$H NMR (D$_2$O):□δ7.70 (s, 1H), 6.28, 6.23 (2×t, 1H), 5.99, 5.96 (dd, 1H, J$_1$=7.6 Hz, J$_2$=2.6 Hz), 5.96–5.99 (dd, 1H, J$_1$=12.9 Hz, J$_2$=3.5 Hz), 4.80–4.90 (2×d, 1H), 4.90, 4.81 (2×d, 1H), 4.52–4.54 (m, 1H), 4.33–4.47 (m, 2H), 4.04–4.17 (m, 4H), 3.96–3.99 (m, 1H), 2.24–2.42 (m, 2H), 1.91 (d, 3H, J=2.3 Hz), 1.86 (s, 3H), 1.44 (2×s, 3H, 9.2 Hz), 1.38 (2×s, 3H), 1.24–1.29 (m, 6H) ppm; $^-$P NMR (D$_2$O): δ59.75, 59.24 ppm.

Nucleoside 1v: $^1$H NMR (D$_2$O): δ7.95 (d, 1H, J=7.9 Hz), 6.25 (t, 1H, J=6.8 Hz), 6.04 (d, 1H, J=7.5 Hz), 4.52–4.55 (m, 1H), 4.42 (t, 1H, J=9.9 Hz), 4.18 (d, 1H, J=2.1 Hz), 2.38–2.43 (m, 1H), 2.12 –2.28 (m, 2H), 1.64–1.79 (m, 2H), 1.06–1.25 (m, 4H), 0.76–0.79 (m, 9H) ppm; $^{31}$P NMR (D$_2$O): δ58.66, 58.61 ppm.

Nucleoside 1x: $^1$H NMR (D$_2$O): δ7.73 (d, 1H, J=5.6 Hz), 6.27 (t, 1H, J=6.8 Hz), 4.54–4.57 (m, 1H), 4.43 (t, 1H, J=9.7 Hz), 4.14 (s, 1H), 4.06–4.09 (m, 2H), 2.31–2.36 (m, 2H), 2.13–2.20 (m, 1H), 1.91 (s, 3H), 1.73–1.79 (m, 1H), 1.64–1.69 (m, 1H), 1.07–1.25 (m, 4H), 0.75–0.79 (m, 9H) ppm; $^{31}$P NMR (D$_2$O): δ58.52, 58.46 ppm.

EXAMPLE 3

Biological Testing of Inhibition of CMV

Selected compounds of the invention were tested against human cytomeglovirus (HCMV). Briefly, a 96 well cell-based assay was used with human foreskin infected with HCMV strain with an MOI of 0.05 plaque forming units per ml. Each well was treated once with a 25 micromolar dose of test compound. Five days following treatment with the test compound, total cellular DNA was harvested after cell lysis. Cell lysates were applied to a Nylon membrane on a dot blot apparatus, the blots hybridized with a probe specific for HCMV DNA, and the blots scanned and analyzed using Scan analysis software. Tested compounds showed significant inhibition of viral growth relative to control samples.

EXAMPLE 4

Biological Testing of Inhibition of HSV-1

Selected compounds of the invention were tested against Herpes Simplex Virus Type 1 (HSV-1). Briefly, a 48 well cell-based assay was used with vero cells infected with HSV-1 strain with an MOI of 0.005 plaque forming units per ml. Each well was treated once with a 25 micromolar dose of test compound at three hours post infection. Two days following treatment with the test compound, plaque reduction was determined to determine cytotoxic compounds. Approximately 30% of the compounds tested were non-cytotoxic in plaque reduction assays.

Cytotoxicity determinations of those compounds of the invention which demonstrated cytotoxicity in plaque reduction assays were then based on a 96 well cell-based assay MTT assays (Sigma). Briefly, 24 h following cells seeded on plates, dilutions of test compounds were added and then incubated for two days in 5% CO2 at 37° C. The MTT assay was then carried out as directed by the manufacturer. Absorbance values were then read at 570 and 600 nm using a multiscan plate reader.

EXAMPLE 5

Biological Testing of Inhibition of HBV

Selected compounds of the invention (W198-10, W198-21, W198-22, and W198-24) were tested against hepatits B virus (HBV):

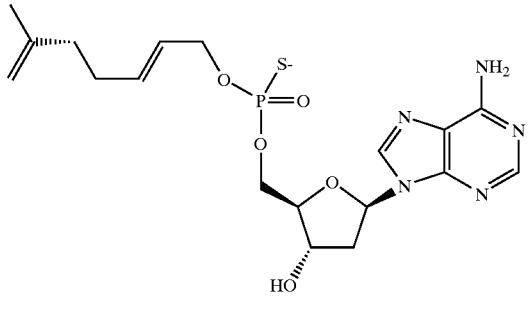

w-198-10

-continued

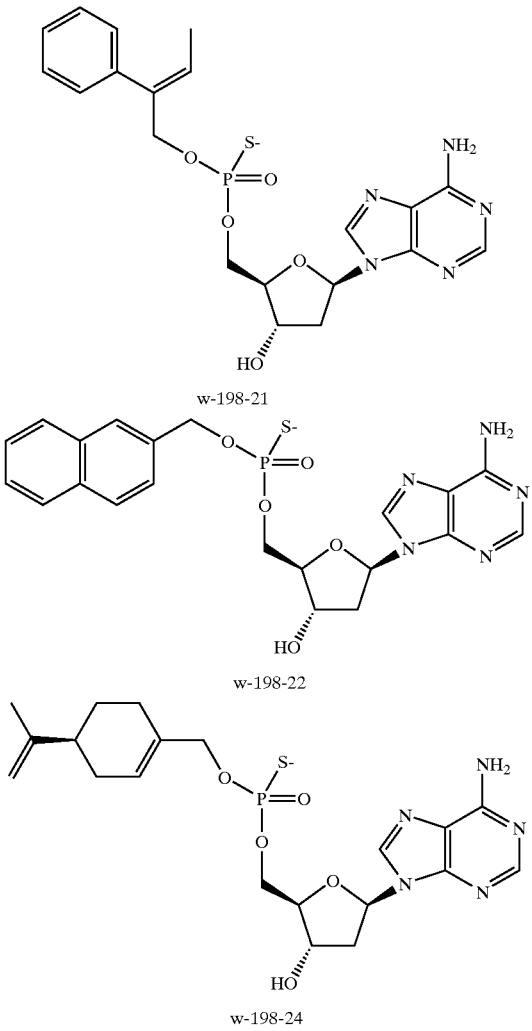

w-198-21 w-198-22 w-198-24

Briefly, confluent 2.2.15 cell cultures infected with an HBV strain were treated with 9 consecutive daily doses of four concentrations of test compound. Extracellular virion HBV DNA levels were followed 24 hours after the last treatment. The level of HBV virion DNA in the 24 control (untreated) cultures in these experiments was 114±16 pg/ml culture medium.

Cells for toxicity analyses were cultured and treated with four concentrations of the test compound. Uptake of neutral red dye was used to determine the relative level of toxicity 24 hours following the last treatment. The absorbance of internalized dye at 510 nm ($A_{510}$) was used for the quantitative analysis. The percentage of dye uptake in the control (untreated) cell cultures was 100±3.

Tested compounds showed significant inhibition of viral growth relative to control samples, with no significant toxicity at concentrations for antiviral activity used, as shown in Tables 3–5.

TABLE 3

Selectivity Indexes of test compounds against HBV replication.

| Compound | $CC_{50}$ ($\mu$M) | $EC_{50}$ ($\mu$M) | $EC_{90}$ ($\mu$M) | Selectivity Index ($CC_{50}/EC_{90}$) |
|---|---|---|---|---|
| W198-10 | >300 | 7.7 ± 0.9 | 24 ± 0.8 | >13 |
| W198-21 | >300 | 5.3 ± 0.6 | 19 ± 2.1 | >16 |
| W198-22 | >300 | 10 ± 1.1 | 32 ± 3.2 | >9.4 |
| W198-24 | >300 | 12 ± 1.2 | 39 ± 4.1 | >7.7 |

TABLE 4

Toxicity analysis of test compounds in 2.2.15 cells.
Neutral Red Dye Uptake at Indicated Drug Concentration (% of control)

| Compound | 300 $\mu$M | 100 $\mu$M | 30 $\mu$M | 10 $\mu$M |
|---|---|---|---|---|
| W198-10 | 98 ± 1 | 99 ± 1 | 102 ± 2 | 100 ± 1 |
| W198-21 | 100 ± 2 | 100 ± 1 | 99 ± 1 | 99 ± 3 |
| W198-22 | 103 ± 2 | 102 ± 2 | 101 ± 3 | 99 ± 2 |
| W198-24 | 102 ± 1 | 103 ± 1 | 102 ± 2 | 100 ± 1 |

TABLE 5

Antiviral analysis of test compounds in 2.2.15 cells.
HBV Virion DNA Levels at indicated Drug Concentration (pg/ml culture)

| Compound | 10 $\mu$M | 1.0 $\mu$M | 0.1 $\mu$M | 0.01 $\mu$M |
|---|---|---|---|---|
| W198-10 | 46 ± 2 | 139 ± 10 | 121 ± 10 | 127 ± 10 |
| W198-21 | 35 ± 4 | 117 ± 12 | 121 ± 13 | 137 ± 14 |
| W198-22 | 59 ± 2 | 152 ± 11 | 122 ± 13 | 129 ± 13 |
| W198-24 | 62 ± 3 | 149 ± 25 | 133 ± 12 | 140 ± 15 |

The invention has been described in detail with reference to preferred embodiments thereof. However, it will be appreciated that those skilled in the art, upon consideration of this disclosure, may make modifications and improvements within the spirit and scope of the invention as set forth in the following claims.

What is claimed is:

1. A compound of the following Formula I or I':

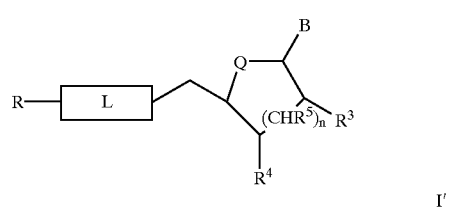

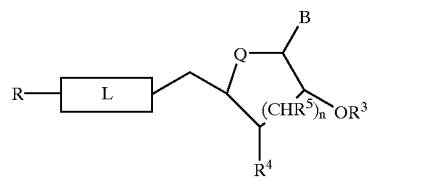

wherein
L is a phosphorothioate, phosphoramidate, thiophosphoramidate, phosphorthioamidate, or phosphordiamidate, and wherein L is optionally substituted with one or more of the same or different $R^1$ groups;

Q is C, O, S or N;

R is a ($C_3$–$C_{12}$) alkyl, a ($C_3$–$C_{12}$) alkenyl, a ($C_3$–$C_{12}$) alkynyl, a ($C_3$–$C_{12}$) aralkyl, a ($C_3$–$C_{12}$) cycloalkyl, a ($C_3$–$C_{12}$) cycloalkenyl, a ($C_3$–$C_{12}$) carbocyclic aryl, or a ($C_3$–$C_{12}$) heteroaromatic or heteroalicyclic group comprising from 1 to 3 separate or fused ring and 1 to 3 N, O or S atoms, wherein R is not a mononucleotide, a substituted mononucleotide, an oligonucleotide, a substituted oligonucleotide, a polynucleotide, or a substituted polynucleotide;

$R^1$, $R^3$, and $R^4$ are each independently selected from a hydrogen or a hydroxyl group or an optionally substituted alkyl, optionally substituted alkenyl, optionally substituted alkynyl, optionally substituted aralkyl, optionally substituted cycloalkyl, optionally substituted cycloalkenyl, optionally substituted carbocyclic aryl, an optionally substituted mononucleotide, an optionally substituted polynucleotide, or an optionally substituted heteroaromatic or heteroalicyclic group preferably having from 1 to 3 separate or fused ring and 1 to 3 N, O or S atoms;

$R^5$ is independently a hydrogen or a hydroxyl group;

B is adenine, thymine, cytosine or guanine, wherein the adenine, thymine, cytosine or guanine are optionally substituted with one or more of the same or different alkyl group, carbocyclic aryl group, heteroaromatic or heteroalicyclic group having from 1 to 3 separate or fused ring and 1 to 3 N, O or S atoms, or a heteroaromatic or heteroalicyclic group other than an adenine, thymine, cytosine or guanine;

n is an integer from 0 to 4;

and enantiomers and pharmaceutically acceptable salts thereof.

2. A compound of the following Formula II or II':

(II)

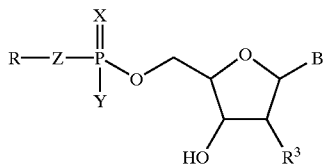

(II')

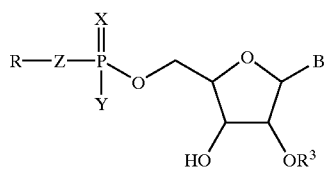

X is O or S and Y is O, S, or N and Z is O or N, wherein Y is S or N when X is O, and Y is O or N when X is S, and wherein X and Y are optionally substituted with one or more of the same or different $R^1$ groups;

R is a ($C_3$–$C_{12}$) alkyl, a ($C_3$–$C_{12}$) alkenyl, a ($C_3$–$C_{12}$) alkynyl, a ($C_3$–$C_{12}$) aralkyl, a ($C_3$–$C_{12}$) cycloalkyl, a ($C_3$–$C_{12}$) cycloalkenyl, a ($C_3$–$C_{12}$) carbocyclic aryl, or a ($C_3$–$C_{12}$) heteroaromatic or heteroalicyclic group having from 1 to 3 separate or fused ring and 1 to 3 N, O or S atoms, wherein R is not a mononucleotide, a substituted mononucleotide, an oligonucleotide, a substituted oligonucleotide, a polynucleotide, or a substituted polynucleotide;

$R^1$ and $R^3$ are each independently selected from a hydrogen or a hydroxyl group or an optionally substituted alkyl, optionally substituted alkenyl, optionally substituted alkynyl, optionally substituted aralkyl, optionally substituted cycloalkyl, optionally substituted cycloalkenyl, optionally substituted carbocyclic aryl, an optionally substituted mononucleotide, an optionally substituted polynucleotide, or an optionally substituted heteroaromatic or heteroalicyclic group preferably having from 1 to 3 separate or fused ring and 1 to 3 N, O or S atoms;

B is adenine, thymine, cytosine or guanine, wherein the adenine, thymine, cytosine or guanine are optionally substituted with one or more of the same or different alkyl group, carbocyclic aryl group, heteroaromatic or heteroalicyclic group having from 1 to 3 separate or fused ring and 1 to 3 N, O or S atoms, or heterocyclic structure covalently linked to the sugar ring;

and enantiomers and pharmaceutically acceptable salts thereof.

3. A compound of the following Formula IIA or IIA':

(IIA)

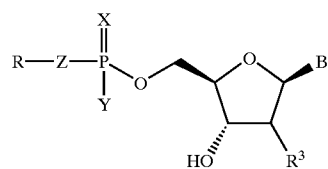

(IIA')

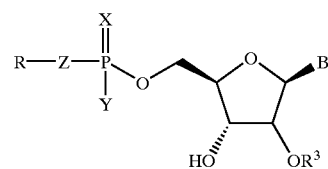

X is O or S and Y is O, S, or N and Z is O or N, wherein Y is S or N when X is O, and Y is O or N when X is S, and wherein X and Y are optionally substituted with one or more of the same or different $R^1$ groups;

R is a ($C_3$–$C_{12}$) alkyl, a ($C_3$–$C_{12}$) alkenyl, a ($C_3$–$C_{12}$) alkynyl, a ($C_3$–$C_{12}$) aralkyl, a ($C_3$–$C_{12}$) cycloalkyl, a ($C_3$–$C_{12}$) cycloalkenyl, a ($C_3$–$C_{12}$) carbocyclic aryl, or a ($C_3$–$C_{12}$) heteroaromatic or heteroalicyclic group having from 1 to 3 separate or fused ring and 1 to 3 N, O or S atoms, wherein R is not a mononucleotide, a substituted mononucleotide, an oligonucleotide, a substituted oligonucleotide, a polynucleotide, or a substituted polynucleotide;

$R^1$ and $R^3$ are each independently selected from a hydrogen or a hydroxyl group or an optionally substituted alkyl, optionally substituted alkenyl, optionally substituted alkynyl, optionally substituted aralkyl, optionally substituted cycloalkyl, optionally substituted cycloalkenyl, optionally substituted carbocyclic aryl, an optionally substituted mononucleotide, an optionally substituted polynucleotide, or an optionally substituted heteroaromatic or heteroalicyclic group preferably having from 1 to 3 separate or fused ring and 1 to 3 N, O or S atoms;

B is adenine, thymine, cytosine or guanine, wherein the adenine, thymine, cytosine or guanine are optionally substituted with one or more of the same or different alkyl group, carbocyclic aryl group, heteroaromatic or heteroalicyclic group having from 1 to 3 separate or fused ring and 1 to 3 N, O or S atoms, or heterocyclic structure covalently linked to the sugar ring;

and enantiomers and pharmaceutically acceptable salts thereof.

4. A compound of claim 1 wherein an enantiomerically enriched mixture of a compound is present.

5. The compound of claim 1 wherein L is an optionally substituted phosphorothioate.

6. The compound of claim 1 wherein L is an optionally substituted thiophosphoramidate.

7. The compound of claim 1 wherein L is an optionally substituted phosphoramidothionate.

8. A pharmaceutical composition comprising a compound of claim 1 and a pharmaceutically acceptable carrier.

9. A method for treating virally infected cells comprising administering to the cells an anti-viral effective amount of a compound of claim 1.

10. The method of claim 9 wherein the cells are infected with a herpes virus.

11. The method of claim 9 wherein the cells are infected with a cytomegalovirus.

12. The method of claim 9 wherein the cells are infected with a hepatitis B virus.

13. A method for treating bacterially infected cells comprising administering to the cells an anti-bacterial effective amount of a compound of claim 1.

14. The method of claim 13 wherein the cells are infected by mycobacterium.

15. A method for treating a mammal suffering from or susceptible to a viral infection, comprising administering to the mammal an anti-viral effective amount of a compound of claim 1.

16. The method of claim 15 wherein the mammal is suffering from a herpes infection.

17. The method of claim 15 wherein the mammal is suffering from a cytomegalovirus infection.

18. The method of claim 15 wherein the mammal is suffering from a hepatitis B virus infection.

19. A method for treating a mammal suffering from or susceptible to a bacterial infection, comprising administering to the mammal an anti-bacterial effective amount of a compound of claim 1.

* * * * *